(12) United States Patent
Zhou

(10) Patent No.: US 12,232,701 B2
(45) Date of Patent: *Feb. 25, 2025

(54) DISPOSABLE SECTION OF ENDOSCOPE HANDLE, ENDOSCOPE HANDLE, AND ENDOSCOPE

(71) Applicant: HUNAN VATHIN MEDICAL INSTRUMENT CO. LTD, Xiangtan (CN)

(72) Inventor: Zhenhua Zhou, Xiamen (CN)

(73) Assignee: HUNAN VATHIN MEDICAL INSTRUMENT CO. LTD, Xiangtan (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/695,823

(22) PCT Filed: Mar. 13, 2023

(86) PCT No.: PCT/CN2023/081138
§ 371 (c)(1),
(2) Date: Mar. 27, 2024

(87) PCT Pub. No.: WO2023/226537
PCT Pub. Date: Nov. 30, 2023

(65) Prior Publication Data
US 2024/0335099 A1    Oct. 10, 2024

(30) Foreign Application Priority Data

May 25, 2022   (CN) ......................... 202210577167.9

(51) Int. Cl.
*A61B 1/00* (2006.01)
*A61B 1/005* (2006.01)
*A61M 25/01* (2006.01)

(52) U.S. Cl.
CPC ........ *A61B 1/0052* (2013.01); *A61B 1/00103* (2013.01); *A61B 1/00105* (2013.01);
(Continued)

(58) Field of Classification Search
CPC ............ A61B 1/00105; A61B 1/00103; A61B 1/00128; A61B 1/0052; A61B 1/0057;
(Continued)

(56) References Cited

U.S. PATENT DOCUMENTS

| | | |
|---|---|---|
| 5,349,942 A | 9/1994 | Heimberger |
| 5,782,748 A | 7/1998 | Palmer et al. |

(Continued)

FOREIGN PATENT DOCUMENTS

| | | |
|---|---|---|
| CN | 105050477 A | 11/2015 |
| CN | 110353612 A | 10/2019 |

(Continued)

*Primary Examiner* — Timothy J Neal
*Assistant Examiner* — James Edward Boice
(74) *Attorney, Agent, or Firm* — Bayramoglu Law Offices LLC

(57) ABSTRACT

A disposable section of an endoscope handle, an endoscope handle, and an endoscope are provided. The disposable section of an endoscope handle includes: a housing provided with a connecting portion that is detachably connected to a reusable section of the handle; an inserting unit including a proximal end located at a distal end of the housing; and a first transmission assembly including: a first traction wire, a second traction wire, and a first connecting element, where the first traction wire and the second traction wire are located in the inserting unit; proximal ends of the first traction wire and the second traction wire are connected to the first connecting element; a proximal end surface of the housing forms a linear movement path that is orthogonal to an axial direction of the proximal end surface; and the first connecting element is movable along the linear movement path.

17 Claims, 7 Drawing Sheets

(52) U.S. Cl.
CPC ..... *A61B 1/00128* (2013.01); *A61M 25/0136* (2013.01); *A61M 25/0147* (2013.01)

(58) Field of Classification Search
CPC ...... A61B 2017/0046; A61M 25/0136; A61M 25/0147
USPC .................................................. 600/131, 197
See application file for complete search history.

(56) References Cited

U.S. PATENT DOCUMENTS

| | | | | |
|---|---|---|---|---|
| 8,177,710 | B1* | 5/2012 | Hosaka | A61B 1/05 600/146 |
| 2006/0069311 | A1* | 3/2006 | Sullivan | A61B 1/0055 600/152 |
| 2011/0295068 | A1* | 12/2011 | Petersen | A61B 1/05 600/131 |
| 2014/0107416 | A1 | 4/2014 | Birnkrant | |
| 2014/0251042 | A1* | 9/2014 | Asselin | F16H 21/40 74/89 |
| 2014/0275763 | A1 | 9/2014 | King et al. | |
| 2017/0086651 | A1* | 3/2017 | Sato | G02B 23/2476 |
| 2017/0188795 | A1 | 7/2017 | Ouyang et al. | |
| 2019/0313881 | A1 | 10/2019 | Francher | |
| 2021/0338052 | A1 | 11/2021 | Ouyang et al. | |

FOREIGN PATENT DOCUMENTS

| | | |
|---|---|---|
| CN | 110730629 A | 1/2020 |
| CN | 110974120 A | 4/2020 |
| CN | 210990141 U | 7/2020 |
| CN | 111920365 A | 11/2020 |
| CN | 112236173 A | 1/2021 |
| CN | 112472002 A | 3/2021 |
| CN | 112790723 A | 5/2021 |
| CN | 114145688 A | 3/2022 |
| CN | 114190866 A | 3/2022 |
| CN | 114795068 A | 7/2022 |
| CN | 114947702 A | 8/2022 |
| JP | H0520704 U | 3/1993 |
| JP | 2006296675 A | 11/2006 |
| JP | 2009148316 A | 7/2009 |
| JP | 2009148420 A | 7/2009 |
| JP | 2009225876 A | 10/2009 |
| WO | 2022001994 A1 | 1/2022 |

* cited by examiner

DISPOSABLE SECTION OF ENDOSCOPE HANDLE, ENDOSCOPE HANDLE, AND ENDOSCOPE

CROSS-REFERENCE TO THE RELATED APPLICATIONS

This application is the national phase entry of International Application No. PCT/CN2023/081138, filed on Mar. 13, 2023, which is based upon and claims priority to Chinese Patent Application No. 202210577167.9, filed on May 25, 2022, the entire contents of which are incorporated herein by reference.

TECHNICAL FIELD

The present disclosure belongs to the technical field of endoscopy and relates to a disposable section of an endoscope handle, an endoscope handle, and an endoscope.

BACKGROUND

An inserting unit, with at least lighting and shooting functions, of an endoscope enters the human body through a natural orifice or a surgical incision to detect the human body's cavity environment. The bending angle of an active bending portion located at the front end of the inserting unit is adjusted through a handle located outside the human body such that the active bending portion is deflected in a preset direction to provide a large visual angle for observation.

Typically, the inserting unit of the endoscope is provided with an instrument channel. Through the instrument channel, excess fluid is extracted from the internal tissue of the human body and exported out of body during the detection or treatment of the human body's cavity environment. In addition, through the instrument channel, external instruments such as biopsy forceps can be delivered into the body cavity to extract a target tissue for biopsy.

When the inserting unit is inserted into the human body, its external part and internal instrument channel are severely contaminated. Typically, after the use, the inserting unit and the handle are discarded as a whole, resulting in high equipment costs for patients. To address the cost issue, in the prior art, the handle is divided into a disposable part and a reusable part. However, the connecting process of the disposable part and the reusable part is complex, increasing the operational difficulty for doctors. Meanwhile, the disposable part needs a new structural design and has a complex force transmission process, resulting in high fabrication costs.

SUMMARY

An objective of the present disclosure is to provide a disposable section of an endoscope handle, including:
- a housing, where the housing is provided with a connecting portion, and the connecting portion is detachably connected to a reusable section of the handle;
- an inserting unit, including a proximal end located at a distal end of the housing; and
- a first transmission assembly, including: a first traction wire, a second traction wire, and a first connecting element, where the first traction wire and the second traction wire are located in the inserting unit; and the first traction wire and the second traction wire include distal ends connected to an active bending portion at a distal end of the inserting unit and proximal ends connected to the first connecting element, where a proximal end surface of the housing forms a linear movement path that is orthogonal to an axial direction of the proximal end surface; and the first connecting element is movable along the linear movement path.

Preferably, the proximal end surface of the housing is provided with a guide groove that is adapted to the linear movement path; and the first connecting element is slidably provided in the guide groove.

Preferably, two ends of the guide groove are respectively provided with a first through-hole and a second through-hole; and the first traction wire and the second traction wire are respectively threaded through the first through-hole and the second through-hole.

Preferably, the two ends of the guide groove are further respectively provided with a first guide mechanism and a second guide mechanism; and the first traction wire and the second traction wire are respectively wound around the first guide mechanism and the second guide mechanism and respectively threaded through the first through-hole and the second through-hole.

Preferably, a proximal end of the housing is detachably provided with a packaging shell; the packaging shell is provided with an accommodating groove that is adapted to a shape of the guide groove and corresponds to the guide groove; and the packaging shell is abutted against the first connecting element along an axial direction of the packaging shell.

Preferably, a width of the guide groove is smaller than a width of the accommodating groove.

The present disclosure further provides an endoscope handle, including the above-mentioned disposable section and reusable section, where the disposable section and the reusable section are detachably connected.

Preferably, a distal end of the reusable section is provided with a second connecting element that is connected to the first connecting element in a matched manner; and the first connecting element is detachably connected to the second connecting element.

Preferably, one of the first connecting element and the second connecting element is a male connecting element, and the other of the first connecting element and the second connecting element is a female connecting element.

The present disclosure further provides an endoscope, including the above-mentioned reusable section of the endoscope handle and the disposable section of the endoscope handle.

Beneficial Effects:

1. In the present disclosure, during a connecting process, an operator only needs to connect the reusable section of the handle to one force transmission component, that is, the first connecting element. The design reduces the difficulty of connecting the reusable section and the disposable section.

2. In the present disclosure, the first connecting element of the disposable section is movable along the linear movement path formed on the proximal end surface of the housing. The present disclosure will not occupy the axial space in the housing. Meanwhile, the first connecting element is connected to the proximal ends of the first traction wire and the second traction wire to form a closed force transmission circuit. Therefore, the present disclosure does not require the stabilizing structure such as the pulley block required by the prior art, saving a large amount of components. Further, in the present disclosure, the disposable section has a simple structure. The first transmission assembly is located on the proximal end surface of the housing, so the occupied internal space of the housing is relatively small, which provides conditions for reducing the size of the housing of the disposable section. Therefore, the present disclosure reduces components, lowers production and processing costs, improves assembly efficiency, enhances production capacity, and reduces the economic burden on patients.

BRIEF DESCRIPTION OF THE DRAWINGS

To describe the technical solutions in the embodiments of the present disclosure more clearly, the following briefly introduces the drawings required for describing the embodiments or the prior art. Apparently, the drawings in the following description show merely some embodiments of the present disclosure, and persons of ordinary skill in the art may still derive other drawings from these drawings without creative efforts.

REFERENCE NUMERALS

Figure 1:
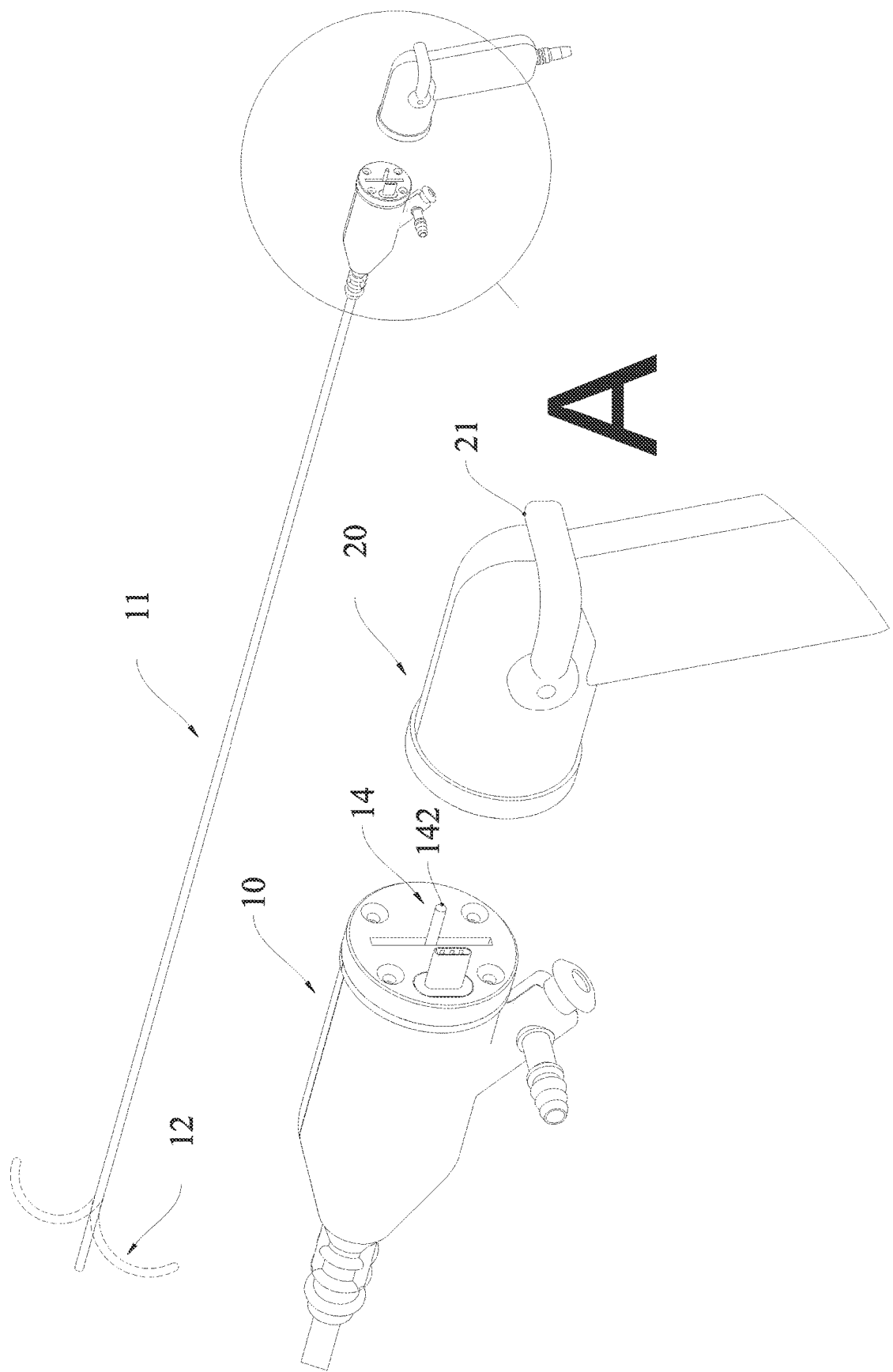
FIG. 1 is an enlarged structural diagram of position A, including a disposable section and a reusable section, of an endoscope handle according to an embodiment of the present disclosure.

10. disposable section; 101. first traction wire; 102. second traction wire; 103. fixing portion; 100. housing; 110. packaging shell; 111. accommodating groove; 112. fixing hole; 11. inserting unit; 12. active bending portion; 13. guide groove; 131. first through-hole; 132. second through-hole; 14. first connecting element; 141. slider; 142. connecting rod; 151. first guide mechanism; 152. second guide mechanism; 150. mounting hole; 20. reusable section; 21. lever; 200. reusable section housing; 22. second connecting element; and 220. connecting hole.

DETAILED DESCRIPTION OF THE EMBODIMENTS

The following description provides many different embodiments or examples for implementing different features of the present disclosure. The elements and arrangements described in the following specific examples are only intended to concisely express the present disclosure, and are only for illustration purposes, rather than to limit the present disclosure.

In order to make the objectives, technical solutions, and advantages of the embodiments of the present disclosure clearer, the technical solutions in the embodiments of the present disclosure will be clearly and completely described below in conjunction with the accompanying drawings in the embodiments of the present disclosure. Obviously, the described embodiments are some, rather than all of the embodiments of the present disclosure. On the basis of the embodiments of the present disclosure, all other embodiments obtained by a person of ordinary skill in the art without making creative efforts shall fall within the protection scope of the present disclosure. Therefore, the detailed description of the embodiments of the present disclosure in the accompanying drawings is not intended to limit the protection scope of the present disclosure, but merely represent the selected embodiments of the present disclosure. On the basis of the embodiments of the present disclosure, all other embodiments obtained by a person of ordinary skill in the art without making creative efforts shall fall within the protection scope of the present disclosure.

In the present disclosure, unless otherwise clearly specified, the terms "installation", "interconnection", "connection" and "fixation" etc. are intended to be understood in a broad sense. For example, the "connection" may be a fixed connection, removable connection or integral connection; may be a mechanical connection or electrical connection; may be a direct connection or indirect connection using a medium; and may be a communication or interaction between two elements. Those of ordinary skill in the art may understand specific meanings of the above terms in the present disclosure based on a specific situation. In addition, the terms such as "first", "second", and "third" are used only for the purpose of description and cannot be understood to indicate or imply relative importance.

In the present disclosure, unless otherwise expressly specified, when it is described that a first feature is "above" or "under" a second feature, it may indicate that the first feature is in direct contact with the second feature, or that the first feature and the second feature are not in direct contact with each other but are in contact via another feature between them. Moreover, "a first feature is above and on a second feature" includes "the first feature is directly above or obliquely above the second feature" or simply means that "the first feature is higher than the second feature". "A first feature is under and below a second feature" includes "the first feature is directly under or obliquely under the second feature" or simply means that "the first feature is lower than the second feature".

In addition, in the present disclosure, for the convenience of describing and understanding the positional relationship between components, "proximal end" and "distal end" refer to proximal and distal positions of a structure for in-vivo operation in an operating environment. For the same component, "proximal end" and "distal end" refer to the relative rather than absolute positional relationship of the component. Therefore, the understanding of "proximal end" and "distal end" should be based on the principles of the present disclosure, without deviating from the essence of the present disclosure.

As shown in FIG. 1, the present disclosure provides disposable section 10 of an endoscope handle.

The disposable section includes housing 100. The housing 100 is provided with a connecting portion. The connecting portion is detachably connected to reusable section 20 of the handle.

Specifically, the connecting portion can be connected to the reusable section 20 of the handle through a clamping area or a clamping element. Alternatively, the connecting portion is connected to the reusable section 20, and the disposable section 10 and the reusable section 20 are connected through a connecting element that can be a threaded collar.

The disposable section includes inserting unit 11. A proximal end of the inserting unit 11 is located at a distal end of the housing 100. A distal end of the inserting unit 11 is provided with active bending portion 12. The active bending portion 12 is bent to detect an internal environment of a human body at different angles.

Figure 2:
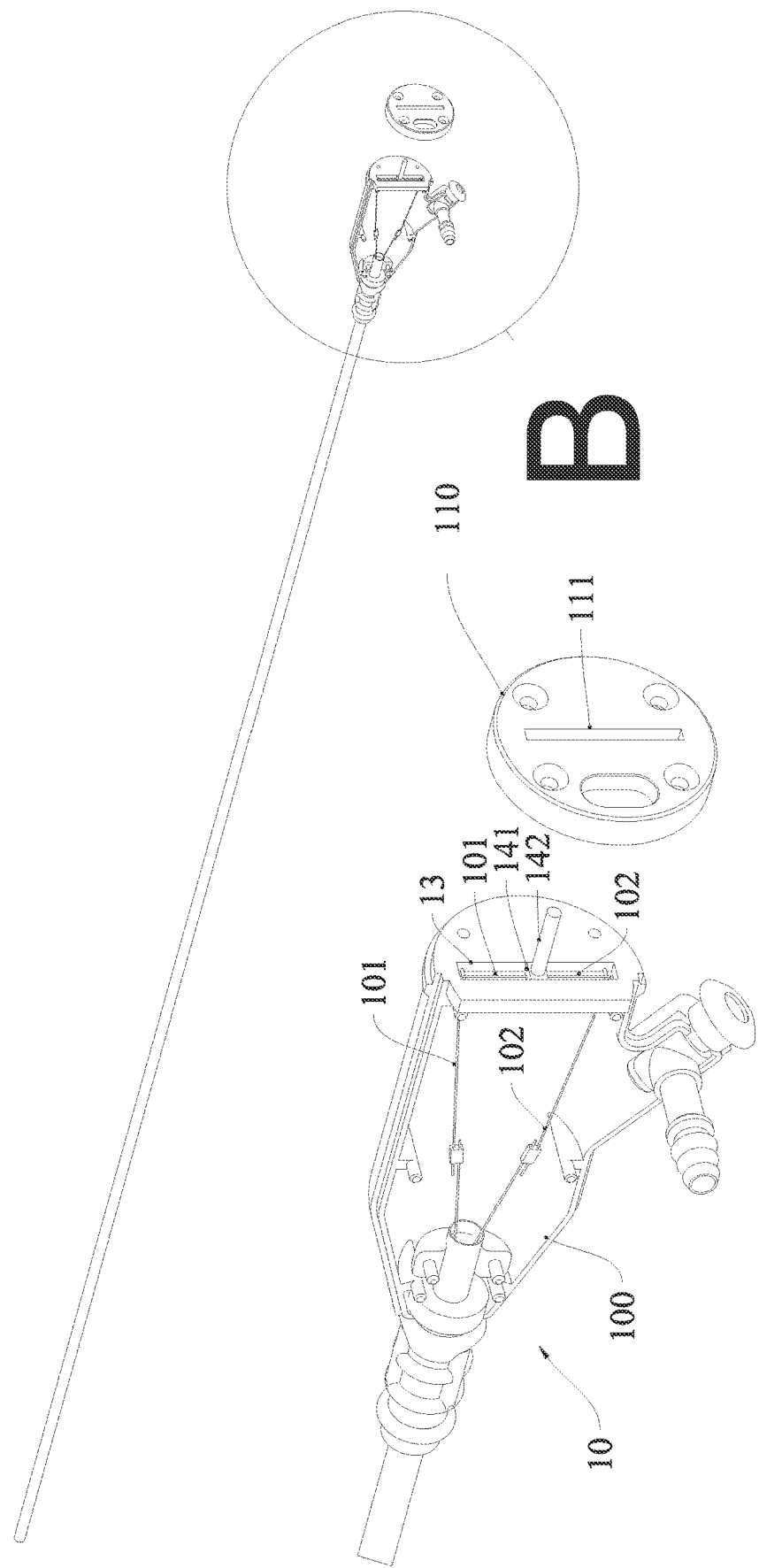
FIG. 2 is an enlarged internal structural diagram of position B of the disposable section of the endoscope handle according to an embodiment of the present disclosure.

As shown in FIG. 2, the disposable section includes a first transmission assembly. The first transmission assembly includes: first traction wire 101, second traction wire 102, and first connecting element 14. The first traction wire 101 and the second traction wire 102 are located in the inserting unit 11. Distal ends of the first traction wire 101 and the second traction wire 102 are connected to the active bending portion 12 at the distal end of the inserting unit 11. The first traction wire 101 and the second traction wire 102 are movable in opposite directions synchronously to deflect and bend the active bending portion 12 in a preset direction, as shown in FIG. 1.

Figure 3:
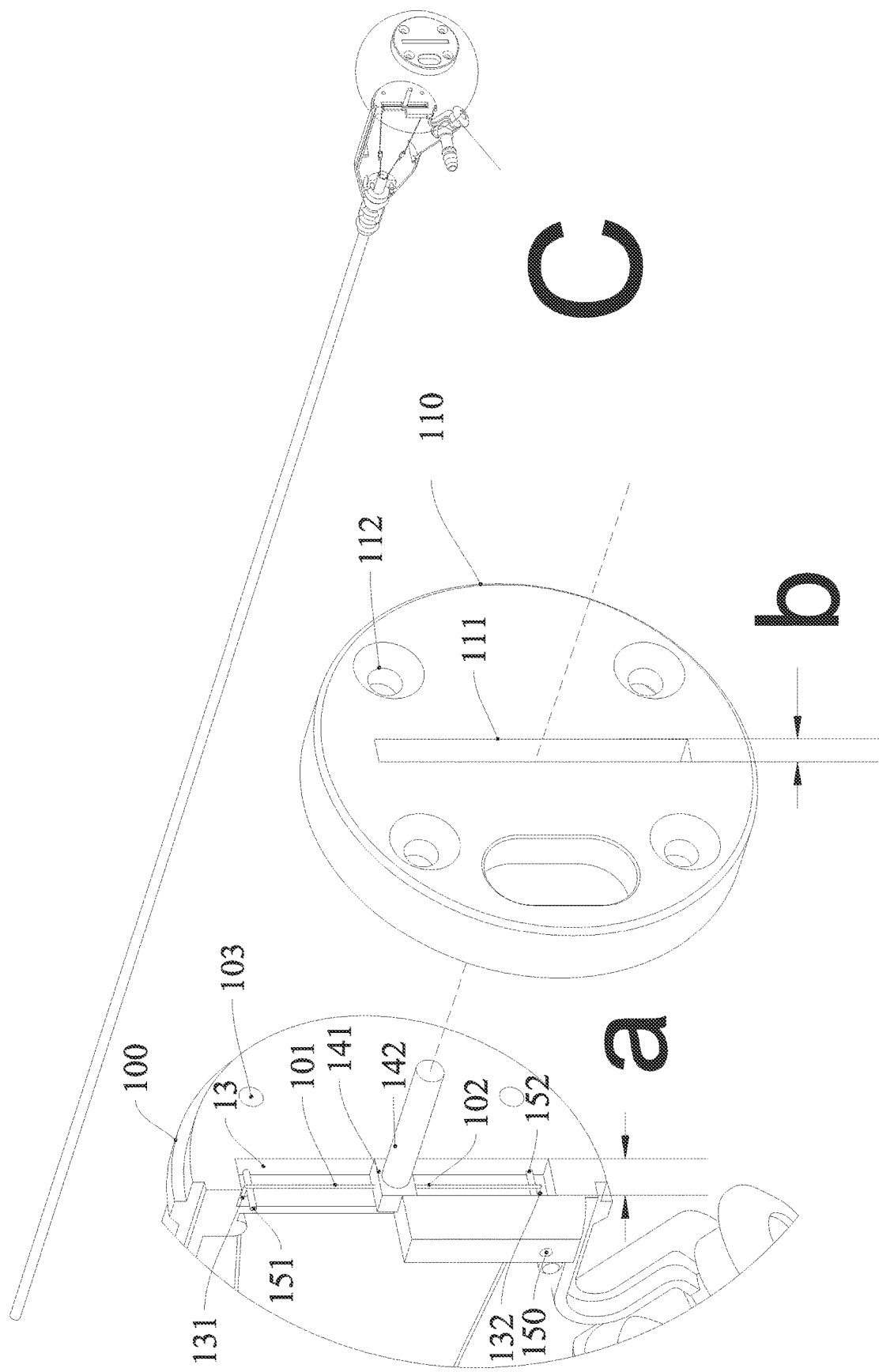
FIG. 3 is an enlarged internal structural diagram of position C of the disposable section of the endoscope handle according to an embodiment of the present disclosure.

As shown in FIGS. 2 and 3, in the disposable section 10 of the endoscope handle provided by the present disclosure, proximal ends of the first traction wire 101 and the second traction wire 102 are connected to the first connecting element 14. A proximal end surface of the housing 100 forms a linear movement path. The linear movement path is orthogonal to an axial direction of the proximal end surface. The first connecting element 14 is movable along the linear movement path. It should be noted that the first traction wire 101, the second traction wire 102, and the first connecting element 14 form a closed force transmission circuit. Therefore, when the first connecting element 14 is forced to move in a forward direction of the linear movement path, the first connecting element 14 drives the first traction wire 101 to move synchronously, thereby driving the second traction wire 102 to move synchronously in the same direction. On the contrary, when the first connecting element 14 is forced to move in a reverse direction of the linear movement path, the first connecting element 14 drives the second traction wire 102 to move synchronously, thereby driving the first traction wire 101 to move synchronously in the same direction.

It should be noted that the linear movement path can be achieved through a structure such as the following implementation.

The proximal end surface of the housing 100 is provided with guide groove 13 that is adapted to the linear movement path. The first connecting element 14 is slidably provided in the guide groove 13. A shape of the guide groove 13 restricts a sliding path of the first connecting element 14 in the guide groove 13. Specifically, the guide groove 13 can be a straight groove, an arc-shaped groove, or a groove of other shape, which is not limited herein. The guide groove 13 is designed to form a trajectory that facilitates the sliding of the first connecting element 14 along the linear movement path and facilitates the mounting of the first connecting element 14. Further, two ends of the guide groove 13 are respectively provided with first through-hole 131 and second through-hole 132. The first traction wire 101 and the second traction wire 102 are respectively threaded through the first through-hole 131 and the second through-hole 132.

Compared with traditional structures, in the present disclosure, the first connecting element 14 moves along a linear movement path formed at the proximal end surface of the housing 100 to transmit a driving force of the reusable section 20 of the endoscope handle. The present disclosure has the following advantages.

1. In the present disclosure, during a connecting process, an operator only needs to connect the reusable section 20 of the handle to one force transmission component, that is, the first connecting element 14. When the first connecting element 14 is forced to move, it directly drives the first traction wire 101 and the second traction wire 102 to move synchronously, ensuring a synchronous movement effect of the first traction wire 101 and the second traction wire 102 and reducing the difficulty of connecting the reusable section 20 and the disposable section 10. It should be noted that in the prior art, at least two force transmission components, typically two push rods, need to be connected. In addition, in the prior art, a signal connector for signal transmission, such as a Type-C connector needs to be connected. However, when there are many connecting positions between the disposable section 10 and the reusable section 20, the connecting difficulty directly increases, and improper application of a force during operation can easily lead to damage to the Type-C connector. Due to the fact that the present disclosure only needs to connect one force transmission component, the connecting difficulty is reduced.

2. Basically, in the prior art, a rod in the disposable part and a rod in the reusable part are connected along an axial direction of the rod. The connecting process involves the connecting positions of the two rods, which increases the connecting difficulty. Besides, when the rod moves along the axial direction, it will occupy the internal space of the disposable part, so it is necessary to design a preset length of space for the rod to move. Meanwhile, to ensure the stability of the rod, the disposable part is typically provided with a pulley block structure to keep the rod in a tight and stable state. However, the stabilizing structure such as the pulley block will occupy the internal space of the disposable part of the housing 100, thereby increasing the difficulty of molding and demolding processes. Due to the specially added pulley block and rod, the overall fabrication cost of the disposable part in the prior art far exceeds that of the disposable section 10 in the present disclosure, which brings huge obstacles to patients who need endoscopy. In response to the above-mentioned technical problems, in the present disclosure, the first connecting element 14 of the disposable section 10 is movable along the linear movement path formed on the proximal end surface of the housing 100. The present disclosure will not occupy the axial space in the housing 100. Meanwhile, the first connecting element 14 is connected to the proximal ends of the first traction wire 101 and the second traction wire 102 to form a closed force transmission circuit. Therefore, the present disclosure does not require the stabilizing structure such as the pulley block required by the prior art, saving a large amount of components. Further, in the present disclosure, the disposable section 10 has a simple structure. The first transmission assembly is located on the proximal end surface of the housing 100, so the occupied internal space of the housing 100 is relatively small, which provides conditions for reducing the size of the housing 100 of the disposable section 10. Therefore, the present disclosure reduces components, lowers production and processing costs, improves assembly efficiency, enhances production capacity, and reduces the economic burden on patients.

In the present disclosure, after the first traction wire 101 and the second traction wire 102 are threaded through the first through-hole 131 and the second through-hole 132, there is a friction between the first traction wire and a wall surface of the first through-hole 131 as well as between the second traction wire and a wall surface of the second through-hole 132. In order to reduce the friction, preferably, the two ends of the guide groove 13 are respectively provided with first guide mechanism 151 and second guide mechanism 152. The first traction wire 101 and the second traction wire 102 are respectively wound around the first guide mechanism 151 and the second guide mechanism 152 and respectively threaded through the first through-hole 131 and the second through-hole 132. Specifically, the first guide mechanism 151 and the second guide mechanism 152 can be roller structures, with respective rollers provided on a side wall of the guide groove 13. The first traction wire 101 and the second traction wire 102 are wound around the first guide mechanism 151 and the second guide mechanism 152 before they are threaded through the first through-hole 131 and the second through-hole 132. The design changes the direction of force transmission between the first traction wire 101 and the second traction wire 102. In addition, the first traction wire 101 and the second traction wire 102 are only threaded through the first through-hole 131 and the second through-hole 132, reducing the friction between the first traction wire 101 and the first through-hole 131 as well as between the second traction wire 102 and the second through-hole 132. Of course, in other embodiments, the first guide mechanism 151 and the second guide mechanism 152 may be smooth arc-shaped surfaces or rods, for the purpose of reducing the friction between the first traction wire 101 and the first guide mechanism 151 as well as between the second traction wire 102 and the second guide mechanism 152 and playing a guiding role. When rods are used for guidance and friction reduction, each rod is inserted and fixed in the guide groove 13 through radial mounting hole 150 provided at a proximal end portion of the housing 100, such that the first traction wire 101 and the second traction wire 102 are respectively threaded through the first through-hole 131 and the second through-hole 132 after they are wounded around the rods.

Figure 4:
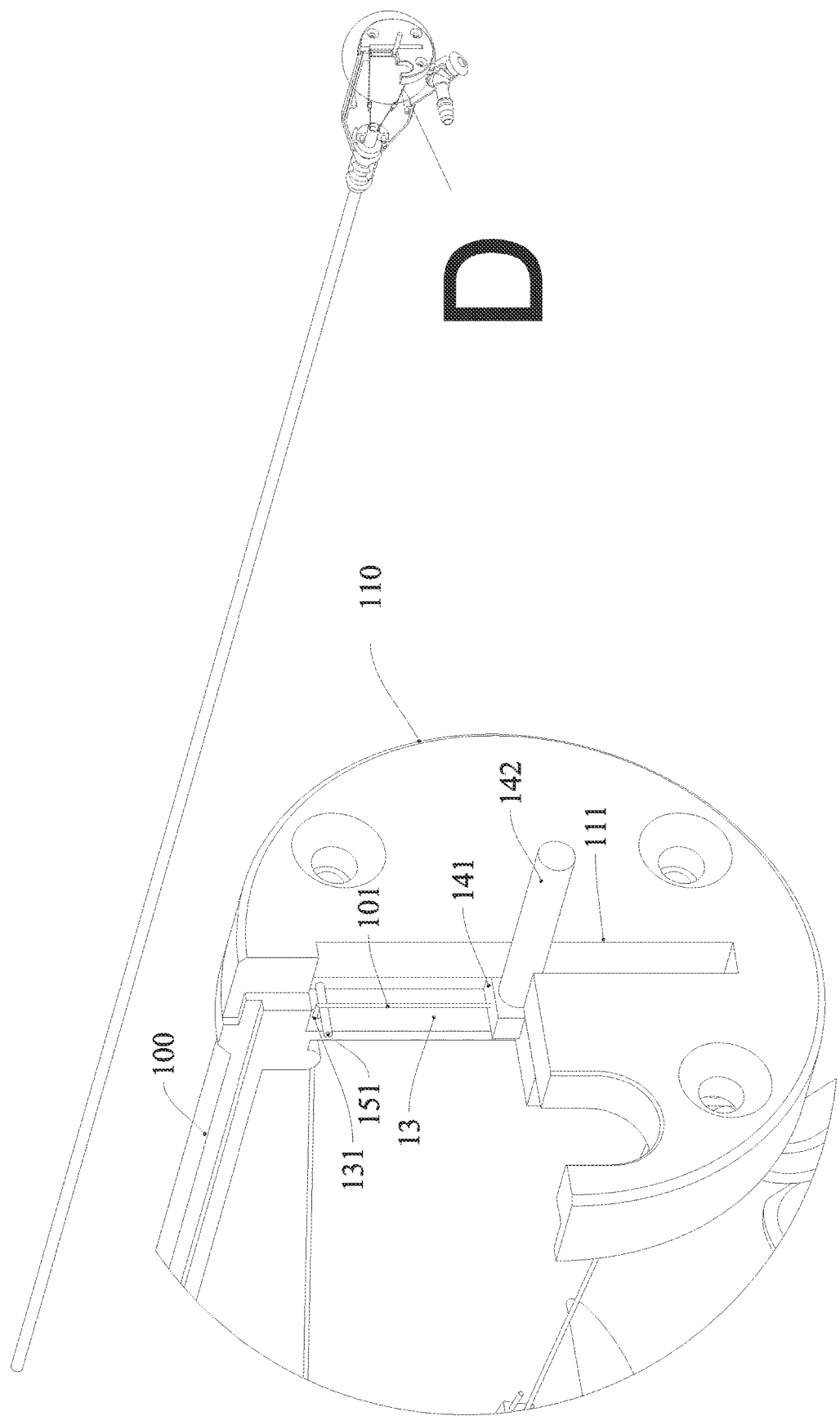
FIG. 4 is an enlarged structural diagram of position D of the disposable section of the endoscope handle according to an embodiment of the present disclosure.

Further, the proximal end of the housing 100 is detachably provided with packaging shell 110. The packaging shell 110 is provided with accommodating groove 111 that is adapted to the shape of the guide groove 13 and corresponds to the guide groove. The packaging shell 110 is abutted against the first connecting element 14 along an axial direction of the packaging shell 110. Specifically, the packaging shell 110 is provided with fixing hole 112. The proximal end surface of the disposable section is provided with fixing portion 103, and the packaging shell 110 is bolted to the fixing portion 103 on the proximal end surface of the disposable section. It should be noted that the packaging shell 110 helps to fix the first connecting element 14 along the axial direction of the disposable section 10, preventing it from being detached. Therefore, in a preferred embodiment, the first connecting element 14 includes slider 141 and connecting rod 142. As shown in FIG. 4, the connecting rod 142 extends along an axial direction of the slider 141 to the proximal end of the disposable section 10 and extends out of the accommodating groove 111 of the packaging shell 110. In this embodiment, a width of the guide groove 13 is adapted to a width of the slider 141 to prevent the slider 141 from moving along a width direction of the guide groove 13. In addition, width b of the accommodating groove 111 is smaller than width a of the guide groove 13. Thus, after the packaging shell 110 and the proximal end of the housing 100 are closed, a side wall of the packaging shell 110 facing the first connecting element 14 is abutted against a proximal end wall surface of the slider 141 along the axial direction of the packaging shell 110. The design can prevent the first connecting element 14 from detaching along the axial direction of the disposable section 10, improving the stability of the first connecting element 14 on the housing 100 such that the first connecting element can only move along the direction of the guide groove 13. It should be noted that in the present disclosure, the first connecting element 14 may also only include the slider 141. The slider 141 is a female connecting element, and the reusable section 20 of the handle is provided with a male connecting element that is matched with the female connecting element to achieve a matched connection.

Figure 5:
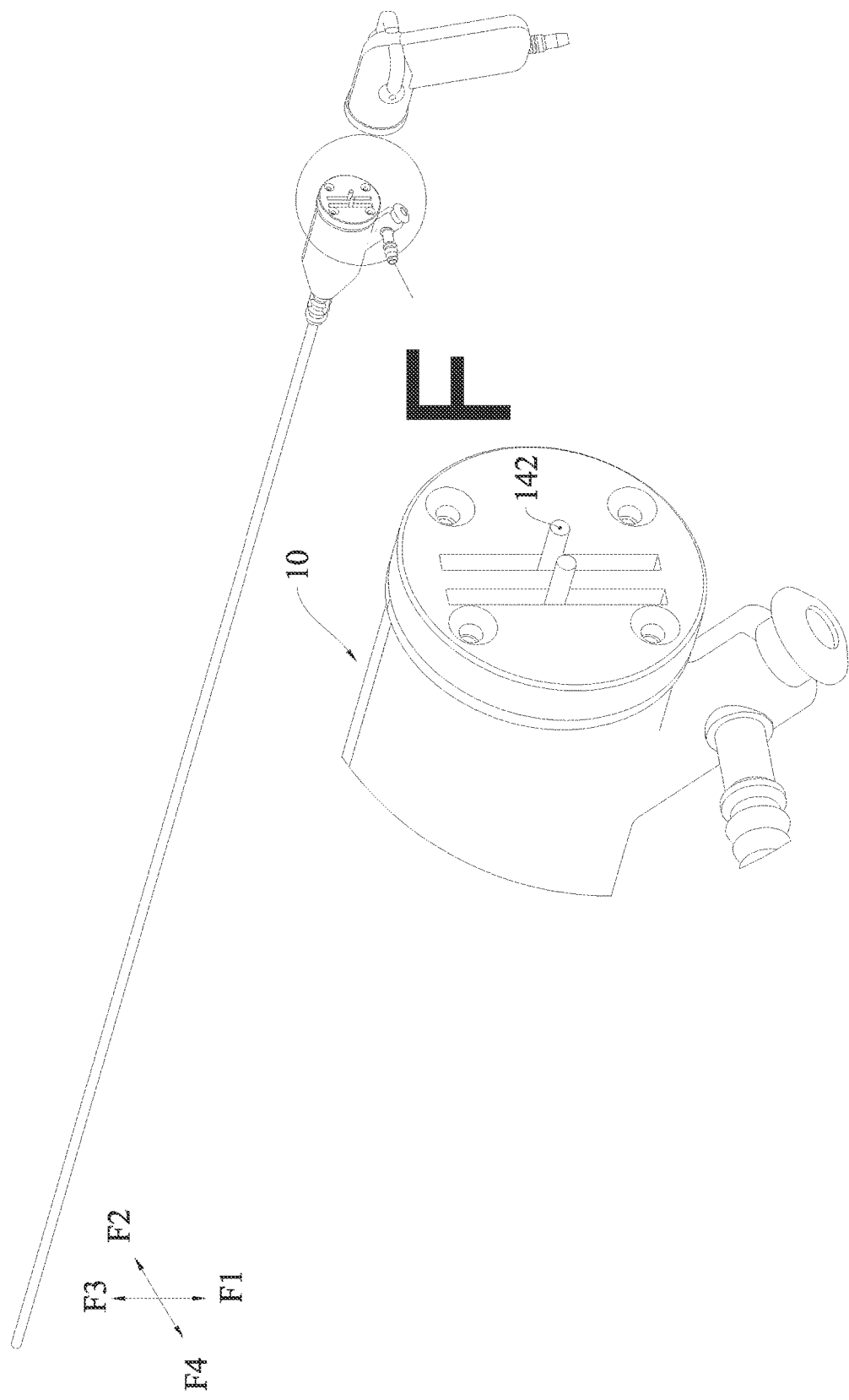
FIG. 5 is an enlarged structural diagram of position F of the endoscope handle according to an embodiment of the present disclosure.
Figure 6:
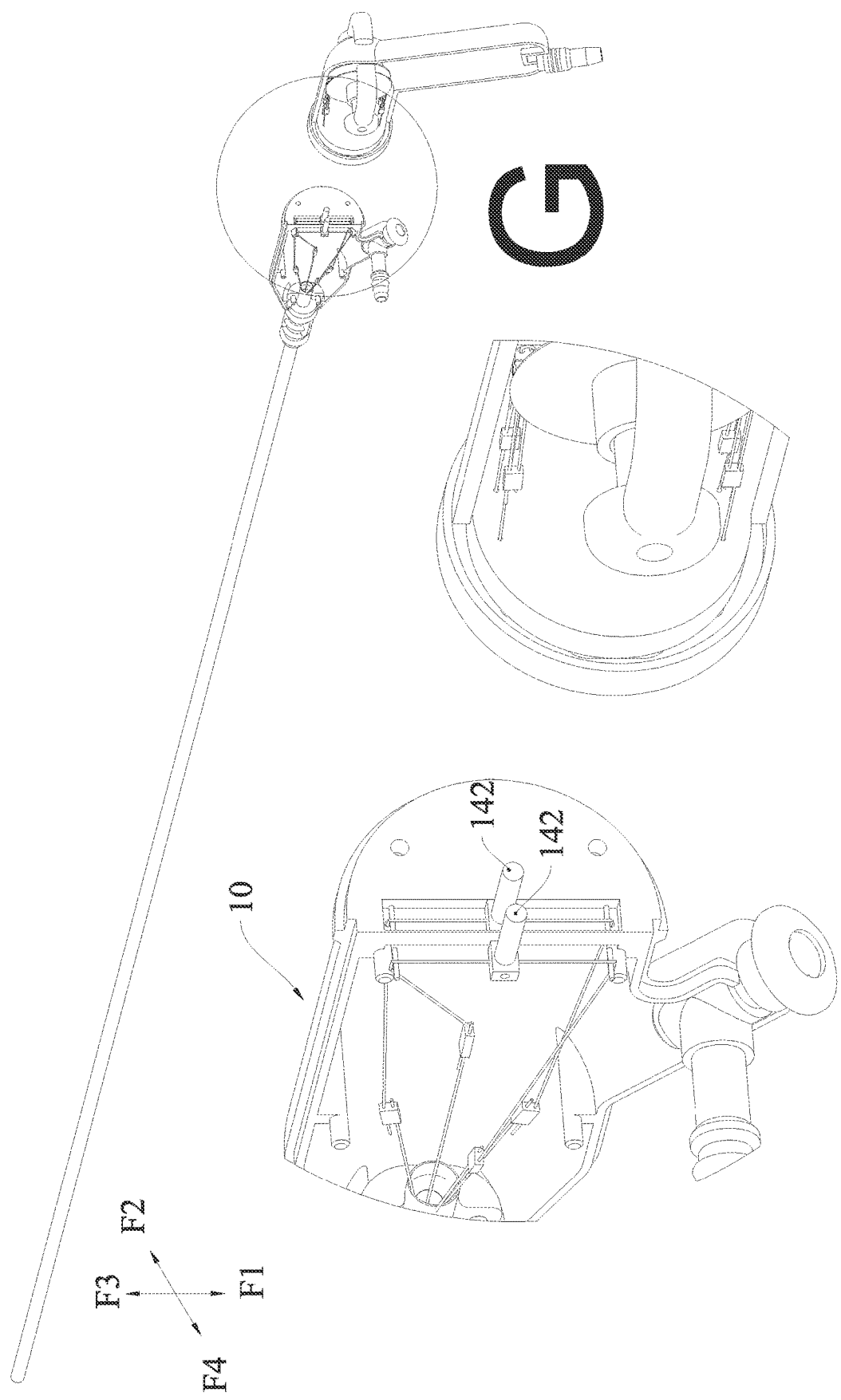
FIG. 6 is an enlarged structural diagram of position G of the endoscope handle according to an embodiment of the present disclosure.

In addition, in the present disclosure, the active bending section of the disposable section 10 can be bent in four directions, namely F1, F2, F3, and F4 shown in FIGS. 5 and 6. For this purpose, the proximal end of the disposable section 10 is provided with two first transmission assemblies, and the proximal end surface of the housing 100 forms two linear movement paths. The two first connecting elements 14 are respectively movable along the two linear movement paths. Specifically, there are two guide grooves 13 on the proximal end of the disposable section 10. The two guide grooves 13 are independent of each other. The reusable section 20 of the handle is provided with two second connecting elements 22. The two second connecting elements 22 are separately driven to achieve the bending of the active bending section in the four directions.

Based on the above-mentioned disposable section 10 of an endoscope handle, the present disclosure further provides an endoscope handle. The disposable section 10 is detachably provided on the reusable section 20 of the handle.

Specifically, the structure of the reusable section 20 of the endoscope handle is as follows.

A distal end of the reusable section 20 is provided with the second connecting element 22 that is connected to the first connecting element 14 in a matched manner, and the first connecting element 14 is detachably connected to the second connecting element 22.

Preferably, one of the first connecting element 14 and the second connecting element 22 is a male connecting element, and the other of the first connecting element 14 and the second connecting element 22 is a female connecting element. Further, the distal end of the reusable section 20 is provided with another linear movement path that is adapted to the linear movement path at the disposable section 10. Specifically, second guide groove 13 is provided at the distal end of the reusable section 20. The second connecting element 22 is located in the second guide groove 13 and slidable along the second guide groove 13.

Figure 7:
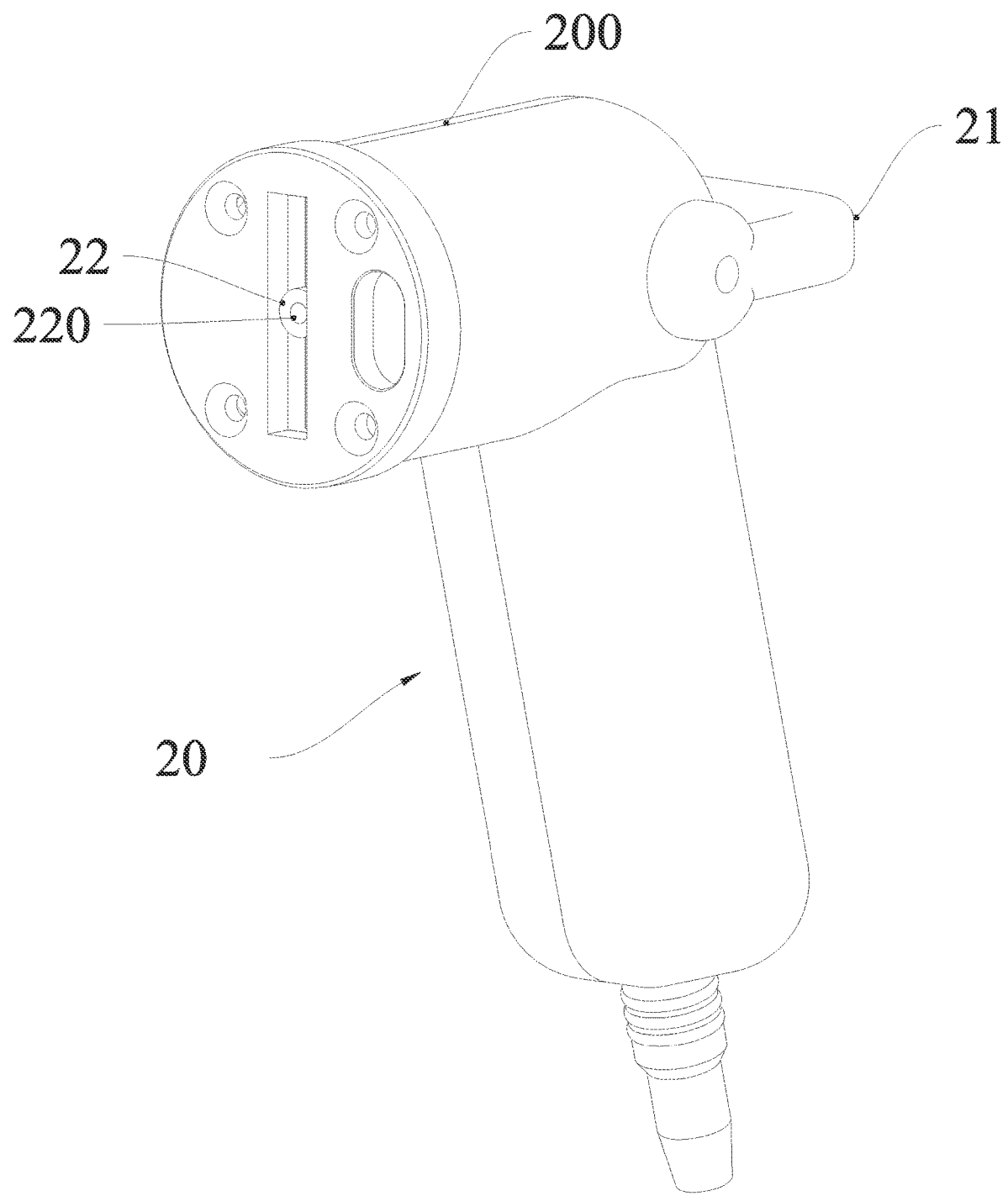
FIG. 7 is a structural diagram of the reusable section of the endoscope handle according to an embodiment of the present disclosure.

As shown in FIG. 7, corresponding to an embodiment of the first connecting element 14 of the above-mentioned disposable section 10, the second connecting element 22 is a female connecting element, and a center of the second connecting element 22 is provided with connecting hole 220 that is connected to the connecting rod 142 of the disposable section 10 in a matched manner. In this way, after the disposable section 10 is connected to the reusable section 20, the second connecting element 22 drives the first connecting element 14 to move, causing the active bending section of the disposable section 10 to bend in a preset direction.

A driving force for driving the second connecting element 22 comes from lever 21, a wheel or other driving component provided on reusable section housing 200.

The present disclosure further provides an endoscope, including the above-mentioned reusable section 20 of an endoscope handle and the disposable section 10 of the endoscope handle.

The above are merely preferred embodiments of the present disclosure, and not intended to limit the present disclosure. Any modifications, equivalent replacements, and improvements made within the spirit and principle of the present disclosure should fall within the protection scope of the present disclosure.

What is claimed is:

1. A disposable section of an endoscope handle, comprising:
- a housing, wherein the housing is provided with a connecting portion, and the connecting portion is detachably connected to a reusable section of the endoscope handle;
- an inserting unit, comprising a proximal end located at a distal end of the housing; and
- a first transmission assembly, comprising: a first traction wire, a second traction wire, and a first connecting element, wherein the first traction wire and the second traction wire are located in the inserting unit; and the first traction wire and the second traction wire comprise distal ends connected to an active bending portion at a distal end of the inserting unit and proximal ends connected to the first connecting element, wherein
- a proximal end surface of the housing forms a linear movement path, the linear movement path is orthogonal to an axial direction of the proximal end surface; and the first connecting element is movable along the linear movement path.

2. The disposable section of the endoscope handle according to claim 1, wherein the proximal end surface of the housing is provided with a guide groove, the guide groove is adapted to the linear movement path; and the first connecting element is slidably provided in the guide groove.

3. The disposable section of the endoscope handle according to claim 2, wherein two ends of the guide groove are respectively provided with a first through-hole and a second through-hole; and the first traction wire and the second traction wire are respectively threaded through the first through-hole and the second through-hole.

4. The disposable section of the endoscope handle according to claim 3, wherein the two ends of the guide groove are further respectively provided with a first guide mechanism and a second guide mechanism; and the first traction wire and the second traction wire are respectively wound around the first guide mechanism and the second guide mechanism and respectively threaded through the first through-hole and the second through-hole.

5. The disposable section of the endoscope handle according to claim 2, wherein a proximal end of the housing is detachably provided with a packaging shell; the packaging shell is provided with an accommodating groove, the accommodating groove is adapted to a shape of the guide groove and corresponds to the guide groove; and the packaging shell is abutted against the first connecting element along an axial direction of the packaging shell.

6. The disposable section of the endoscope handle according to claim 5, wherein a width of the guide groove is smaller than a width of the accommodating groove.

7. An endoscope handle, comprising the disposable section of the endoscope handle according to claim 1 and the reusable section of the endoscope handle, wherein the disposable section of the endoscope handle and the reusable section of the endoscope handle are detachably connected.

8. The endoscope handle according to claim 7, wherein
- a distal end of the reusable section is provided with a second connecting element, the second connecting element is connected to the first connecting element in a matched manner; and the first connecting element is detachably connected to the second connecting element.

9. The endoscope handle according to claim 8, wherein a first one of the first connecting element and the second connecting element is a male connecting element, and a second one of the first connecting element and the second connecting element is a female connecting element.

10. An endoscope, comprising the endoscope handle according to claim 7.

11. An endoscope handle, comprising the disposable section of the endoscope handle according to claim 2 and the reusable section of the endoscope handle, wherein the disposable section of the endoscope handle and the reusable section of the endoscope handle are detachably connected.

12. An endoscope handle, comprising the disposable section of the endoscope handle according to claim 3 and the reusable section of the endoscope handle, wherein the disposable section of the endoscope handle and the reusable section of the endoscope handle are detachably connected.

13. An endoscope handle, comprising the disposable section of the endoscope handle according to claim 4 and the reusable section of the endoscope handle, wherein the disposable section of the endoscope handle and the reusable section of the endoscope handle are detachably connected.

14. An endoscope handle, comprising the disposable section of the endoscope handle according to claim 5 and the reusable section of the endoscope handle, wherein the disposable section of the endoscope handle and the reusable section of the endoscope handle are detachably connected.

15. An endoscope handle, comprising the disposable section of the endoscope handle according to claim 6 and the reusable section of the endoscope handle, wherein the disposable section of the endoscope handle and the reusable section of the endoscope handle are detachably connected.

16. An endoscope, comprising the endoscope handle according to claim 8.

17. An endoscope, comprising the the endoscope handle according to claim 9.

* * * * *